(12) United States Patent
Pilla et al.

(10) Patent No.: US 7,758,490 B2
(45) Date of Patent: Jul. 20, 2010

(54) INTEGRATED COIL APPARATUS FOR THERAPEUTICALLY TREATING HUMAN AND ANIMAL CELLS, TISSUES AND ORGANS WITH ELECTROMAGNETIC FIELDS AND METHOD FOR USING SAME

(75) Inventors: Arthur A. Pilla, Oakland, NJ (US); Andre' DiMino, Woodcliff Lake, NJ (US); Iyer Viswanathan, Santa Clara, CA (US)

(73) Assignee: Ivivi Health Sciences, LLC, San Francisco, CA (US)

( * ) Notice: Subject to any disclaimer, the term of this patent is extended or adjusted under 35 U.S.C. 154(b) by 1210 days.

(21) Appl. No.: 11/223,073

(22) Filed: Sep. 10, 2005

(65) Prior Publication Data

US 2007/0060981 A1   Mar. 15, 2007

(51) Int. Cl.
*A61N 1/00*   (2006.01)
(52) U.S. Cl. .......................................................... 600/13
(58) Field of Classification Search ................ 600/9–15
See application file for complete search history.

(56) References Cited

U.S. PATENT DOCUMENTS 4,993,413 A * 2/1991 McLeod et al. ................ 607/2
5,478,303 A * 12/1995 Foley-Nolan et al. ......... 600/15

* cited by examiner

*Primary Examiner*—John P Lacyk
(74) *Attorney, Agent, or Firm*—Shay Glenn LLP (57) ABSTRACT

An apparatus and method for electromagnetic treatment for treatment of molecules, cells, tissues, and organs comprising: configuring at least one waveform according to a mathematical model having at least one waveform parameter, said at least one waveform to be coupled to a target pathway structure; choosing a value of said at least one waveform parameter so that said at least waveform is configured to be detectable in said target pathway structure above background activity in said target pathway structure; generating an electromagnetic signal from said configured at least one waveform; and coupling said electromagnetic signal to said target pathway structure using a coupling device wherein said coupling device is an integral portion of a positioning device.

98 Claims, 7 Drawing Sheets

Figure 5: PMF pre-treatment increases neuronal survival after serum withdrawal

INTEGRATED COIL APPARATUS FOR THERAPEUTICALLY TREATING HUMAN AND ANIMAL CELLS, TISSUES AND ORGANS WITH ELECTROMAGNETIC FIELDS AND METHOD FOR USING SAME

BACKGROUND OF THE INVENTION

1. Field of the Invention

This invention pertains generally to an electromagnetic treatment integrated coil apparatus and a method for using same to achieve modification of cellular and tissue growth, repair, maintenance, and general behavior by application of encoded electromagnetic information. More particularly this invention relates to the application of surgically non-invasive coupling of highly specific electromagnetic signal patterns to any number of body parts. This invention also relates to treatment of living tissues and cells by altering their interaction with their electromagnetic environment. The invention further relates to a method of modification of cellular and tissue growth, repair, maintenance, and general behavior by the application of encoded electromagnetic information. In particular, an embodiment according to the present invention pertains to using an induction means such as a coil to deliver pulsing electromagnetic fields ("PEMF") to enhance living tissue growth and repair integrated with devices such as supports, wraps, beds, and wheelchairs, and in conjunction with other therapeutic and wellness physical modalities, such as ultrasound, negative or positive pressure, heat, cold, massage.

2. Discussion of Related Art

It is now well established that application of weak non-thermal electromagnetic fields ("EMF") can result in physiologically meaningful in vivo and in vitro bioeffects.

EMF has been used in applications of bone repair and bone healing. Waveforms comprising low frequency components and low power are currently used in orthopedic clinics. Origins of using bone repair signals began by considering that an electrical pathway may constitute a means through which bone can adaptively respond to EMF signals. A linear physicochemical approach employing an electrochemical model of a cell membrane predicted a range of EMF waveform patterns for which bioeffects might be expected. Since a cell membrane was a likely EMF target, it became necessary to find a range of waveform parameters for which an induced electric field could couple electrochemically at the cellular surface, such as voltage-dependent kinetics. Extension of this linear model also involved Lorentz force analysis.

A pulsed radio frequency ("PRF") signal derived from a 27.12 MHz continuous sine wave used for deep tissue healing is known in the prior art of diathermy. A pulsed successor of the diathermy signal was originally reported as an electromagnetic field capable of eliciting a non-thermal biological effect in the treatment of infections. PRF therapeutic applications have been reported for reduction of post-traumatic and post-operative pain and edema in soft tissues, wound healing, burn treatment and nerve regeneration. Application of EMF for the resolution of traumatic edema has become increasingly used in recent years. Results to date using PRF in animal and clinical studies suggest that edema may be measurably reduced from such electromagnetic stimulus.

Prior art considerations of EMF dosimetry have not taken into account dielectric properties of tissue structure as opposed to the properties of isolated cells.

In recent years, clinical use of non-invasive PRF at radio frequencies comprised using pulsed bursts of a 27.12 MHz sinusoidal wave, wherein each pulse burst comprises a width of sixty-five microseconds, having approximately 1,700 sinusoidal cycles per burst, and various burst repetition rates. This limited frequency components that could couple to relevant dielectric pathways in cells and tissue.

Time-varying electromagnetic fields, comprising either rectangular, pseudo-rectangular, or both rectangular and pseudo-rectangular waveforms, such as pulse modulated electromagnetic fields, and sinusoidal waveforms such as pulsed radio frequency fields ranging from several Hertz to an about 15 to an about 40 MHz range, are clinically beneficial when used as an adjunctive therapy for a variety of musculoskeletal injuries and conditions.

Beginning in the 1960's, development of modern therapeutic and prophylactic devices was stimulated by clinical problems associated with non-union and delayed union bone fractures. Early work showed that an electrical pathway can be a means through which bone adaptively responds to mechanical input. Early therapeutic devices used implanted and semi-invasive electrodes delivering direct current ("DC") to a fracture site. Non-invasive technologies were subsequently developed using electrical and electromagnetic fields. These modalities were originally created to provide a non-invasive "no-touch" means of inducing an electrical/mechanical waveform at a cell/tissue level. Clinical applications of these technologies in orthopaedics have led to approved applications by regulatory bodies worldwide for treatment of fractures such as non-unions and fresh fractures, as well as spine fusion. Presently several EMF devices constitute the standard armamentarium of orthopaedic clinical practice for treatment of difficult to heal fractures. The success rate for these devices has been very high. The database for this indication is large enough to enable its recommended use as a safe, non-surgical, non-invasive alternative to a first bone graft. Additional clinical indications for these technologies have been reported in double blind studies for treatment of avascular necrosis, tendinitis, osteoarthritis, wound repair, blood circulation and pain from arthritis as well as other musculoskeletal injuries.

Cellular studies have addressed effects of weak low frequency electromagnetic fields on both signal transduction pathways and growth factor synthesis. It can be shown that EMF stimulates secretion of growth factors after a short, trigger-like duration. Ion/ligand binding processes at a cell membrane are generally considered an initial EMF target pathway structure. The clinical relevance to treatments for example of bone repair, is upregulation such as modulation, of growth factor production as part of normal molecular regulation of bone repair. Cellular level studies have shown effects on calcium ion transport, cell proliferation, Insulin Growth Factor ("IGF-II") release, and IGF-II receptor expression in osteoblasts. Effects on Insulin Growth Factor-I ("IGF-I") and IGF-II have also been demonstrated in rat fracture callus. Stimulation of transforming growth factor beta ("TGF-β") messenger RNA ("mRNA") with PEMF in a bone induction model in a rat has been shown. Studies have also demonstrated upregulation of TGF-β mRNA by PEMF in human osteoblast-like cell line designated MG-63, wherein there were increases in TGF-β1, collagen, and osteocalcin synthesis. PEMF stimulated an increase in TGF-β1 in both hypertrophic and atrophic cells from human non-union tissue. Further studies demonstrated an increase in both TGF-β1 mRNA and protein in osteoblast cultures resulting from a direct effect of EMF on a calcium/calmodulin-dependent pathway. Cartilage cell studies have shown similar increases in TGF-β1 mRNA and protein synthesis from EMF, demonstrating a therapeutic application to joint repair. Various studies conclude that upregulation of growth factor production may be a common denominator in the tissue level mechanisms underlying electromagnetic stimulation. When using specific inhibitors, EMF can act through a calmodulin-dependent pathway. It has been previously reported that specific PEMF and PRF signals, as well as weak static magnetic fields, modulate $Ca^{2+}$ binding to CaM in a cell-free enzyme preparation. Additionally, upregulation of mRNA for BMP2 and BMP4 with PEMF in osteoblast cultures and upregulation of TGF-$\beta$1 in bone and cartilage with PEMF have been demonstrated.

However, prior art in this field does not use an induction apparatus that delivers a signal according to a mathematical model, is programmable, lightweight, portable, disposable, implantable, and configured with, integrated into, or attached to at least one of garments, fashion accessories, footware, bandages, anatomical supports, an anatomical wraps, apparel, cushions, mattresses, pads, wheelchairs, therapeutic beds, therapeutic chairs, therapeutic and health maintenance devices such as vacuum assisted wound closure devices, mechanical and functional electrical stimulation devices and exercise devices, ultrasound, heat, cold, massage, and exercise. A further need exists for an electromagnetic treatment induction apparatus and a method for using same that is lightweight, portable, implantable, and can be disposable. A further need exists for an electromagnetic treatment induction apparatus and method having decreased power requirements and non-invasive characteristics that allow an enhanced signal to be integrated into surgical dressings, wound dressings, pads, seat cushions, mattress pads, shoes, and any other garment and structure juxtaposed to living tissue and cells, even to be integral to creation of a garment to deliver an enhanced EMF signal to any body parts and that delivers a signal according to a mathematical model and is programmable.

SUMMARY OF THE INVENTION

An electromagnetic treatment induction apparatus integrated into therapeutic and non-therapeutic devices and a method for using same for therapeutic treatment of living tissues and cells by inductively coupling optimally configured waveforms to alter the living tissues and cells' interaction with their electromagnetic environment.

According to an embodiment of the present invention, by treating a selectable body region with a flux path comprising a succession of EMF pulses having a minimum width characteristic of at least about 0.01 microseconds in a pulse burst envelope having between about 1 and about 100,000 pulses per burst, in which a voltage amplitude envelope of said pulse burst is defined by a randomly varying parameter in which instantaneous minimum amplitude thereof is not smaller than the maximum amplitude thereof by a factor of one ten-thousandth. The pulse burst repetition rate can vary from about 0.01 to about 10,000 Hz. A mathematically definable parameter can also be employed to define an amplitude envelope of said pulse bursts.

By increasing a range of frequency components transmitted to relevant cellular pathways, access to a large range of biophysical phenomena applicable to known healing mechanisms, including enhanced enzyme activity and growth factor and cytokine release, is advantageously achieved.

According to an embodiment of the present invention, by applying a random, or other high spectral density envelope, to a pulse burst envelope of mono- or bi-polar rectangular or sinusoidal pulses which induce peak electric fields between $10^{-6}$ and 10 volts per centimeter (V/cm), a more efficient and greater effect can be achieved on biological healing processes applicable to both soft and hard tissues in humans, animals and plants. A pulse burst envelope of higher spectral density can advantageously and efficiently couple to physiologically relevant dielectric pathways, such as, cellular membrane receptors, ion binding to cellular enzymes, and general transmembrane potential changes thereby modulating angiogenesis and neovascularization.

By advantageously applying a high spectral density voltage envelope as a modulating or pulse-burst defining parameter, power requirements for such modulated pulse bursts can be significantly lower than that of an unmodulated pulse. This is due to more efficient matching of the frequency components to the relevant cellular/molecular process. Accordingly, the dual advantages of enhanced transmitting dosimetry to relevant dielectric pathways and of decreasing power requirements are achieved.

A preferred embodiment according to the present invention utilizes a Power Signal to Noise Ratio ("Power SNR") approach to configure bioeffective waveforms and incorporates miniaturized circuitry and lightweight flexible coils. This advantageously allows a device that utilizes a Power SNR approach, miniaturized circuitry, and lightweight flexible coils, to be completely portable and if desired to be constructed as disposable and if further desired to be constructed as implantable. The lightweight flexible coils can be an integral portion of a positioning device such as surgical dressings, wound dressings, pads, seat cushions, mattress pads, shoes, wheelchairs, chairs, and any other garment and structure juxtaposed to living tissue and cells. By advantageously integrating a coil into a positioning device therapeutic treatment can be provided to living tissue and cells in an inconspicuous and convenient manner.

Specifically, broad spectral density bursts of electromagnetic waveforms, configured to achieve maximum signal power within a bandpass of a biological target, are selectively applied to target pathway structures such as living organs, tissues, cells and molecules. Waveforms are selected using a unique amplitude/power comparison with that of thermal noise in a target pathway structure. Signals comprise bursts of at least one of sinusoidal, rectangular, chaotic and random wave shapes, have frequency content in a range of about 0.01 Hz to about 100 MHz at about 1 to about 100,000 bursts per second, and have a burst repetition rate from about 0.01 to about 1000 bursts/second. Peak signal amplitude at a target pathway structure such as tissue, lies in a range of about 1 $\mu$V/cm to about 100 mV/cm. Each signal burst envelope may be a random function providing a means to accommodate different electromagnetic characteristics of healing tissue. A preferred embodiment according to the present invention comprises about 0.1 to about 100 millisecond pulse burst comprising about 1 to about 200 microsecond symmetrical or asymmetrical pulses repeating at about 0.1 to about 100 kilohertz within the burst. The burst envelope is a modified 1/f function and is applied at random repetition rates between about 0.1 and about 1000 Hz. Fixed repetition rates can also be used between about 0.1 Hz and about 1000 Hz. An induced electric field from about 0.001 mV/cm to about 100 mV/cm is generated. Another embodiment according to the present invention comprises an about 0.01 millisecond to an about 10 millisecond burst of high frequency sinusoidal waves, such as 27.12 MHz, repeating at about 1 to about 100 bursts per second. An induced electric field from about 0.001 mV/cm to about 100 mV/cm is generated. Resulting waveforms can be delivered via inductive or capacitive coupling.

It is another object of the present invention to provide an electromagnetic method of treatment of living cells and tissues comprising a broad-band, high spectral density electromagnetic field.

It is a further object of the present invention to provide an electromagnetic method of treatment of living cells and tissues comprising amplitude modulation of a pulse burst envelope of an electromagnetic signal that will induce coupling with a maximum number of relevant EMF-sensitive pathways in cells or tissues.

It is an object of the present invention to configure a power spectrum of a waveform by mathematical simulation by using signal to noise ratio ("SNR") analysis to configure a waveform optimized to modulate angiogensis and neovascualarization then coupling the configured waveform using a generating device such as ultra lightweight wire coils that are powered by a waveform configuration device such as miniaturized electronic circuitry.

It is an object of the present invention to provide lightweight flexible coils, that can be integrated into at least one of garments, fashion accessories, footwear, bandages, anatomical supports, an anatomical wraps, apparel, cushions, mattresses, pads, wheelchairs, therapeutic beds, therapeutic chairs, therapeutic and health maintenance devices such as vacuum assisted wound closure devices, mechanical and functional electrical stimulation devices and exercise devices and dressings to deliver the optimum dose of non-invasive pulsed electromagnetic treatment configured as shown above, for enhanced repair and growth of living tissue in animals, humans and plants.

It is another object of the present invention to deliver a waveform configured by SNR/Power analysis of a target pathway structure, in a programmable manner for example according to a time-dose program, a series of pulses, or some other sequence random or patterned.

It is another object of the present invention to generate a signal from a waveform configured by SNR/Power analysis of a target pathway structure, in a programmable manner for example according to a time-dose program, a series of pulses, or some other sequence random or patterned.

It is another object of the present invention to provide multiple coils, delivering a waveform configured by SNR/Power analysis of a target pathway structure, to increase area of treatment coverage.

It is another object of the present invention to provide multiple coils that are simultaneously driven or that are sequentially driven such as multiplexed, with the same or different optimally configured waveforms as shown above.

It is a further object of the present invention to provide flexible, lightweight coils that focus the EMF signal to the affected tissue by incorporating the coils, delivering a waveform configured by SNR/Power analysis of a target pathway structure, into ergonomic support garments.

It is yet a further object of the present invention to utilize conductive thread to create daily wear, and exercise and sports garments having integrated coils, delivering a waveform configured by SNR/Power analysis of a target pathway structure, positioned in proximity to an anatomical target.

It is yet a further object of the present invention to utilize lightweight flexible coils or conductive thread to deliver the EMF signal to affected tissue by incorporating such coils or conductive threads as an integral part of various types of bandages, such as, compression, elastic, cold compress and hot compress and delivering a waveform configured by SNR/Power analysis of a target pathway structure.

It is another object of the present invention to employ several coils, delivering a waveform configured by SNR/Power analysis of a target pathway structure, to increase EMF coverage area.

It is another object of the present invention to construct a coil, delivering a waveform configured by SNR/Power analysis of a target pathway structure, using conductive thread.

It is another object of the present invention to construct a coil, delivering a waveform configured by SNR/Power analysis of a target pathway structure, using fine flexible conductive wire.

It is another object of the present invention to supply the same or different waveforms configured by SNR/Power analysis of a target pathway structure, simultaneously or sequentially to single or multiple coils.

It is yet a further object of the present invention to incorporate at least one coil in a surgical wound dressing to apply an enhanced EMF signal non-invasively and non-surgically, the surgical wound dressing to be used in combination with standard wound treatment.

It is another object of the present invention to construct the coils delivering a waveform configured by SNR/Power analysis of a target pathway structure, for easy attachment and detachment to dressings, garments and supports by using an attachment means such as Velcro, an adhesive and any other such temporary attachment means.

It is another object of the present invention to provide coils delivering a waveform configured by SNR/Power analysis of a target pathway structure, that are integrated with therapeutic beds, therapeutic chairs, and wheelchairs.

It is another object of the present invention to provide coils delivering a waveform configured by SNR/Power analysis of a target pathway structure, that are integrated with various therapy surfaces, such as pressure relieving, inflatable, fluid, visco-elastic and air fluidized bed and other support surfaces.

It is another object of the present invention to provide coils delivering a waveform configured by SNR/Power analysis of a target pathway structure that are integrated with therapeutic seat cushions such as inflatable, fluidized, foam cushions.

It is another object of the present invention to provide coils delivering a waveform configured by SNR/Power analysis of a target pathway structure, that are integrated with at least one of therapeutic mattress overlays, sheets, blankets, pillows, pillow cases, and therapeutic devices that can apply steady or intermittent pressure such as air clearance vests.

It is another object of the present invention to provide for the inclusion of a flux path to any therapeutic surface, structure, or device to enhance the effectiveness of such therapeutic surfaces, structures or devices by delivering a waveform configured by SNR/Power analysis of a target pathway structure.

It is another object of the present invention to incorporate coils delivering a waveform configured by SNR/Power analysis of a target pathway structure, in footware such as shoes.

It is another object of the present invention to integrate at least one coil delivering a waveform configured by SNR/Power analysis of a target pathway structure, with a therapeutic surface, structure or device to enhance the effectiveness of such therapeutic surface, structure or device.

It is yet another object of the present invention to integrate at least one coil delivering a waveform configured by Power SNR analysis of a target pathway structure, with at least one of a therapeutic surface, a therapeutic structure, and a therapeutic device, to enhance the effectiveness of the at least one of the therapeutic surface, the therapeutic structure, and the therapeutic device, to prevent the loss and deterioration of cells and tissues.

It is yet another object of the present invention to integrate at least one coil delivering a waveform configured by Power SNR analysis of a target pathway structure, with at least one of a therapeutic surface, a therapeutic structure, and a therapeutic device, to enhance the effectiveness of the at least one of the therapeutic surface, the therapeutic structure, and the therapeutic device, to augment cell and tissue activity.

It is yet another object of the present invention to integrate at least one coil delivering a waveform configured by Power SNR analysis of a target pathway structure, with at least one of a therapeutic surface, a therapeutic structure, and a therapeutic device, to enhance the effectiveness of the at least one of the therapeutic surface, the therapeutic structure, and the therapeutic device, to increase cell population.

It is yet another object of the present invention to integrate at least one coil delivering a waveform configured by Power SNR analysis of a target pathway structure, with at least one of a therapeutic surface, a therapeutic structure, and a therapeutic device, to enhance the effectiveness of the at least one of the therapeutic surface, the therapeutic structure, and the therapeutic device, to prevent neuron deterioration.

It is yet another object of the present invention to integrate at least one coil delivering a waveform configured by Power SNR analysis of a target pathway structure, with at least one of a therapeutic surface, a therapeutic structure, and a therapeutic device, to enhance the effectiveness of the at least one of the therapeutic surface, the therapeutic structure, and the therapeutic device, to increase neuron population.

It is yet another object of the present invention to integrate at least one coil delivering a waveform configured by Power SNR analysis of a target pathway structure, with at least one of a therapeutic surface, a therapeutic structure, and a therapeutic device, to enhance the effectiveness of the at least one of the therapeutic surface, the therapeutic structure, and the therapeutic device, to prevent deterioration of adrenergic neurons in a cerebrofacial area.

It is yet another object of the present invention to integrate at least one coil delivering a waveform configured by Power SNR analysis of a target pathway structure, with at least one of a therapeutic surface, a therapeutic structure, and a therapeutic device, to enhance the effectiveness of the at least one of the therapeutic surface, the therapeutic structure, and the therapeutic device, to increase adrenergic neuron population in a cerebrofacial area.

The above and yet other objects and advantages of the present invention will become apparent from the hereinafter set forth Brief Description of the Drawings, Detailed Description of the Invention, and Claims appended herewith.

BRIEF DESCRIPTION OF THE DRAWINGS

Preferred embodiments of the present invention will be described below in more detail, with reference to the accompanying drawings.

DETAILED DESCRIPTION

Induced time-varying currents from PEMF or PRF devices flow in a target pathway structure such as a molecule, cell, tissue, and organ, and it is these currents that are a stimulus to which cells and tissues can react in a physiologically meaningful manner. The electrical properties of a target pathway structure affect levels and distributions of induced current. Molecules, cells, tissue, and organs are all in an induced current pathway such as cells in a gap junction contact. Ion or ligand interactions at binding sites on macromolecules that may reside on a membrane surface are voltage dependent processes, that is electrochemical, that can respond to an induced electromagnetic field ("E"). Induced current arrives at these sites via a surrounding ionic medium. The presence of cells in a current pathway causes an induced current ("J") to decay more rapidly with time ("J(t)"). This is due to an added electrical impedance of cells from membrane capacitance and time constants of binding and other voltage sensitive membrane processes such as membrane transport.

Equivalent electrical circuit models representing various membrane and charged interface configurations have been derived. For example, in Calcium ("$Ca^{2+}$") binding, the change in concentration of bound $Ca^{2+}$ at a binding site due to induced E may be described in a frequency domain by an impedance expression such as:

$$Z_b(\omega) = R_{ion} + \frac{1}{i\omega C_{ion}}$$

which has the form of a series resistance-capacitance electrical equivalent circuit. Where $\omega$ is angular frequency defined as $2\pi f$, where f is frequency, $i=-1^{1/2}$, $Z_b(\omega)$ is the binding impedance, and $R_{ion}$ and $C_{ion}$ are equivalent binding resistance and capacitance of an ion binding pathway. The value of the equivalent binding time constant, $\tau_{ion}=R_{ion}C_{ion}$, is related to a ion binding rate constant, $k_b$, via $\tau_{ion}=R_{ion}C_{ion}=1/k_b$. Thus, the characteristic time constant of this pathway is determined by ion binding kinetics.

Induced E from a PEMF or PRF signal can cause current to flow into an ion binding pathway and affect the number of $Ca^{2+}$ ions bound per unit time. An electrical equivalent of this is a change in voltage across the equivalent binding capacitance $C_{ion}$, which is a direct measure of the change in electrical charge stored by $C_{ion}$. Electrical charge is directly proportional to a surface concentration of $Ca^{2+}$ ions in the binding site, that is storage of charge is equivalent to storage of ions or other charged species on cell surfaces and junctions. Electrical impedance measurements, as well as direct kinetic analyses of binding rate constants, provide values for time constants necessary for configuration of a PMF waveform to match a bandpass of target pathway structures. This allows for a required range of frequencies for any given induced E waveform for optimal coupling to target impedance, such as bandpass.

Ion binding to regulatory molecules is a frequent EMF target, for example $Ca^{2+}$ binding to calmodulin ("Car"). Use of this pathway is based upon acceleration of tissue repair, for example bone repair, wound repair, hair repair, and repair of other molecules, cells, tissues, and organs that involves modulation of growth factors released in various stages of repair. Growth factors such as platelet derived growth factor ("PDGF"), fibroblast growth factor ("FGE"), and epidermal growth factor ("EGF") are all involved at an appropriate stage of healing. Angiogenesis and neovascularization are also integral to tissue growth and repair and can be modulated by PMF. All of these factors are Ca/CaM-dependent.

Utilizing a Ca/CaM pathway a waveform can be configured for which induced power is sufficiently above background thermal noise power. Under correct physiological conditions, this waveform can have a physiologically significant bioeffect.

Application of a Power SNR model to Ca/CaM requires knowledge of electrical equivalents of $Ca^{2+}$ binding kinetics at CaM. Within first order binding kinetics, changes in concentration of bound $Ca^{2+}$ at CaM binding sites over time may be characterized in a frequency domain by an equivalent binding time constant, $\tau_{ion}=R_{ion}C_{ion}$, where $R_{ion}$ and $C_{ion}$ are equivalent binding resistance and capacitance of the ion binding pathway. $\tau_{ion}$ is related to a ion binding rate constant, $k_b$, via $\tau_{ion}=R_{ion}C_{ion}=1/k_b$. Published values for $k_b$ can then be employed in a cell array model to evaluate SNR by comparing voltage induced by a PRF signal to thermal fluctuations in voltage at a CaM binding site. Employing numerical values for PMF response, such as $V_{max}=6.5\times10^{-7}$ $sec^{-1}$, $[Ca^{2+}]=2.5$ μM, $K_D=30$ μM, $[Ca^{2+}CaM]=K_D([Ca^{2+}]+[CaM])$, yields $k_b=665$ $sec^{-1}$ ($\tau_{ion}=1.5$ msec). Such a value for $\tau_{ion}$ can be employed in an electrical equivalent circuit for ion binding while power SNR analysis can be performed for any waveform structure.

According to an embodiment of the present invention a mathematical model can be configured to assimilate that thermal noise is present in all voltage dependent processes and represents a minimum threshold requirement to establish adequate SNR. Power spectral density, $S_n(\omega)$, of thermal noise can be expressed as:

$$S_n(\omega)=4kT\,Re[Z_M(x,\omega)]$$

where $Z_M(x,\omega)$ is electrical impedance of a target pathway structure, x is a dimension of a target pathway structure and Re denotes a real part of impedance of a target pathway structure. $Z_M(x,\omega)$ can be expressed as:

$$Z_M(x,\omega)=\left[\frac{R_e+R_i+R_g}{\gamma}\right]\tanh(\gamma x)$$

This equation clearly shows that electrical impedance of the target pathway structure, and contributions from extracellular fluid resistance ("$R_e$"), intracellular fluid resistance ("$R_i$") and intermembrane resistance ("$R_g$") which are electrically connected to target pathway structures, all contribute to noise filtering.

A typical approach to evaluation of SNR uses a single value of a root mean square (RMS) noise voltage. This is calculated by taking a square root of an integration of $S_n(\omega)=4$ kT Re[$Z_M(x,\omega)$] over all frequencies relevant to either complete membrane response, or to bandwidth of a target pathway structure. SNR can be expressed by a ratio:

$$SNR=\frac{|V_M(\omega)|}{RMS}$$

where $|V_M(\omega)|$ is maximum amplitude of voltage at each frequency as delivered by a chosen waveform to the target pathway structure.

An embodiment according to the present invention comprises a pulse burst envelope having a high spectral density, so that the effect of therapy upon the relevant dielectric pathways, such as, cellular membrane receptors, ion binding to cellular enzymes and general transmembrane potential changes, is enhanced. Accordingly by increasing a number of frequency components transmitted to relevant cellular pathways, a large range of biophysical phenomena, such as modulating growth factor and cytokine release and ion binding at regulatory molecules, applicable to known tissue growth mechanisms is accessible. According to an embodiment of the present invention applying a random, or other high spectral density envelope, to a pulse burst envelope of mono- or bi-polar rectangular or sinusoidal pulses inducing peak electric fields between about $10^{-8}$ and about 100 V/cm, produces a greater effect on biological healing processes applicable to both soft and hard tissues.

According to yet another embodiment of the present invention by applying a high spectral density voltage envelope as a modulating or pulse-burst defining parameter, power requirements for such amplitude modulated pulse bursts can be significantly lower than that of an unmodulated pulse burst containing pulses within a similar frequency range. This is due to a substantial reduction in duty cycle within repetitive burst trains brought about by imposition of an irregular, and preferably random, amplitude onto what would otherwise be a substantially uniform pulse burst envelope. Accordingly, the dual advantages, of enhanced transmitted dosimetry to the relevant dielectric pathways and of decreased power requirement are achieved.

Figure 1:
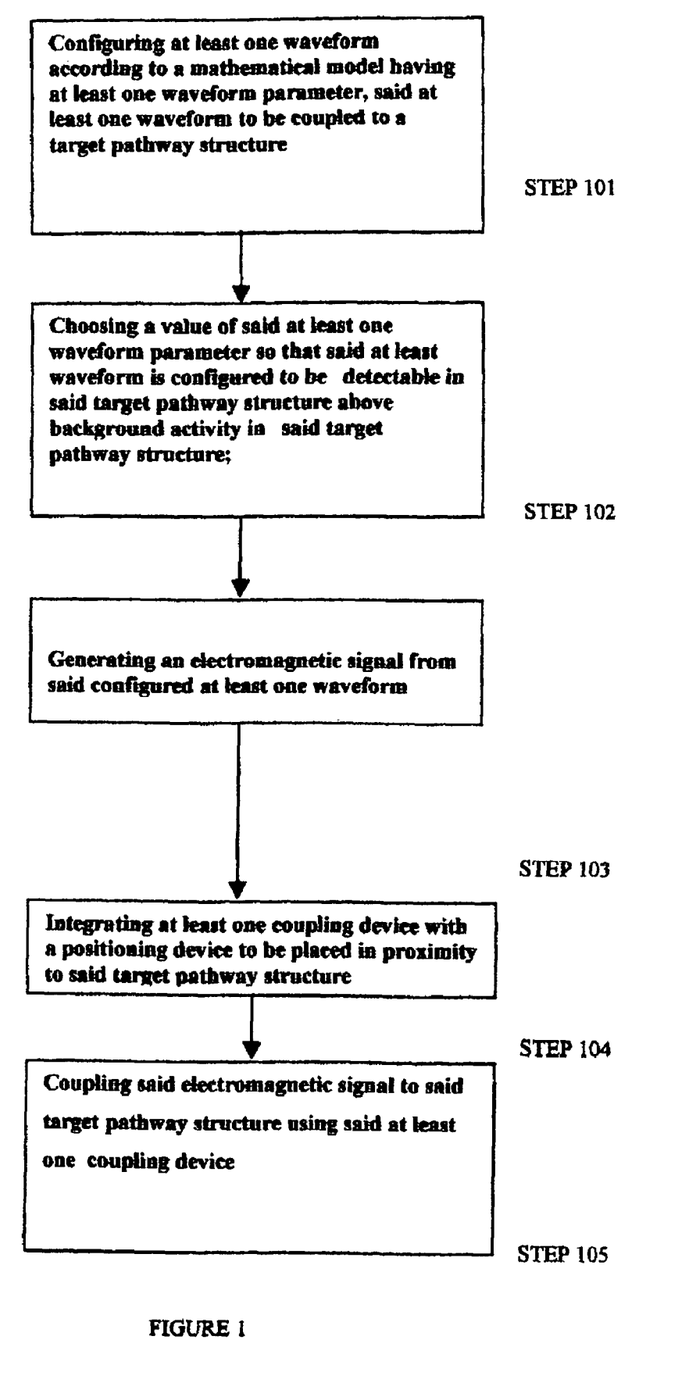
FIG. 1 is a flow diagram of a electromagnetic therapeutic treatment method for using coils integrated into a positioning device according to an embodiment of the present invention.

Referring to FIG. 1, wherein FIG. 1 is a flow diagram of a method for delivering electromagnetic signals to tissue target pathway structures such as ions and ligands of animals, and humans for therapeutic and prophylactic purposes according to an embodiment of the present invention. A mathematical model having at least one waveform parameter is applied to configure at least one waveform to be coupled to target pathway structures such as ions and ligands (Step 101). The configured waveform satisfies a Power SNR model so that for a given and known target pathway structure it is possible to choose at least one waveform parameter so that a waveform is detectable in the target pathway structure above its background activity (Step 102) such as baseline thermal fluctuations in voltage and electrical impedance at a target pathway structure that depend upon a state of a cell and tissue, that is whether the state is at least one of resting, growing, replacing, and responding to injury.

A preferred embodiment of a generated electromagnetic signal is comprised of a burst of arbitrary waveforms having at least one waveform parameter that includes a plurality of frequency components ranging from about 0.01 Hz to about 100 MHz wherein the plurality of frequency components satisfies a Power SNR model (Step 102). A repetitive electromagnetic signal can be generated for example inductively or capacitively, from said configured at least one waveform (Step 103). The electromagnetic signal is coupled to a target pathway structure such as ions and ligands by output of a coupling device such as an electrode or an inductor, placed in close proximity to the target pathway structure (Step 104) using a positioning device by integrating the coupling device with the positioning device (Step 105). The coupling enhances modulation of binding of ions and ligands to regulatory molecules tissues, cells, and organs. The coupling, device can be integrated into the structure of the positioning device. The positioning device can be surgical dressings, wound dressings, pads, seat cushions, mattress pads, shoes, wheelchairs, chairs, and any other garment and structure that can be juxtaposed to living tissue and cells. An advantage of integrating the coupling device with a positioning device is that therapeutic treatment can be administered in an unnoticeable fashion and can be administered anywhere and at anytime.

Figure 2:
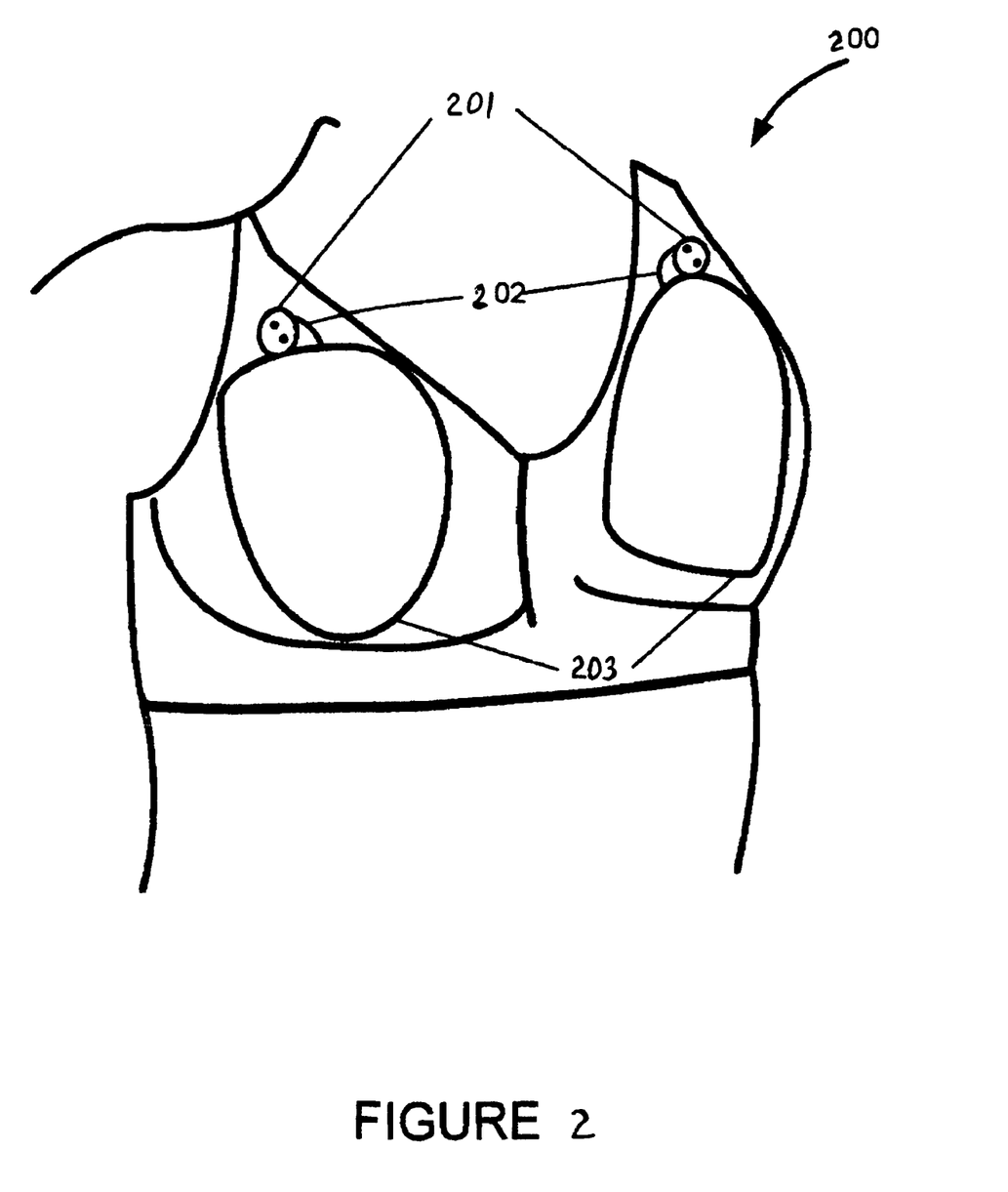
FIG. 2 is a view of an electromagnetic treatment apparatus according to a preferred embodiment of the present invention.

FIG. 2 illustrates a preferred embodiment of an apparatus according to the present invention. The apparatus is self-contained, lightweight, and portable. A miniature control circuit 201 is coupled to an end of at least one connector 202 such as wire however the control circuit can also operate wirelessly. The opposite end of the at least one connector is coupled to a generating device such as an electrical coil 203. The miniature control circuit 201 is constructed in a manner that applies a mathematical model that is used to configure waveforms. The configured waveforms have to satisfy a Power SNR model so that for a given and known target pathway structure, it is possible to choose waveform parameters that satisfy Power SNR so that a waveform is detectable in the target pathway structure above its background activity. A preferred embodiment according to the present invention applies a mathematical model to induce a time-varying magnetic field and a time-varying electric field in a target pathway structure such as ions and ligands, comprising about 0.1 to about 100 msec bursts of about 1 to about 100 microsecond rectangular pulses repeating at about 0.1 to about 100 pulses per second. Peak amplitude of the induced electric field is between about 1 uV/cm and about 100 mV/cm, varied according to a modified 1/f function where f=frequency. A waveform configured using a preferred embodiment according to the present invention may be applied to a target pathway structure such as ions and ligands for a preferred total exposure time of under 1 minute to 240 minutes daily. However other exposure times can be used. Waveforms configured by the miniature control circuit 201 are directed to a generating device 203 such as electrical coils via connector 202. The generating device 203 delivers a pulsing magnetic field configured according to a mathematical model that can be used to provide treatment to a target pathway structure such as skin tissue. The miniature control circuit applies a pulsing magnetic field for a prescribed time and can automatically repeat applying the pulsing magnetic field for as many applications as are needed in a given time period, for example 10 times a day. The miniature control circuit can be configured to be programmable applying pulsing magnetic fields for any time repetition sequence. A preferred embodiment according to the present invention can be positioned to treat hair 204 by being incorporated with a positioning device thereby making the unit self-contained. Coupling a pulsing magnetic field to a target pathway structure such as ions and ligands, therapeutically and prophylactically reduces inflammation thereby reducing pain and promotes healing in treatment areas. When electrical coils are used as the generating device 203, the electrical coils can be powered with a time varying magnetic field that induces a time varying electric field in a target pathway structure according to Faraday's law. An electromagnetic signal generated by the generating device 203 can also be applied using electrochemical coupling, wherein electrodes are in direct contact with skin or another outer electrically conductive boundary of a target pathway structure. Yet in another embodiment according to the present invention, the electromagnetic signal generated by the generating device 203 can also be applied using electrostatic coupling wherein an air gap exists between a generating device 203 such as an electrode and a target pathway structure such as ions and ligands. An advantage of the preferred embodiment according to the present invention is that its ultra lightweight coils and miniaturized circuitry allow for use with common physical therapy treatment modalities and at any location for which tissue growth, pain relief, and tissue and organ healing is desired. An advantageous result of application of the preferred embodiment according to the present invention is that tissue growth, repair, and maintenance can be accomplished and enhanced anywhere and at anytime. Yet another advantageous result of application of the preferred embodiment is that growth, repair, and maintenance of molecules, cells, tissues, and organs can be accomplished and enhanced anywhere and at anytime.

Figure 3:
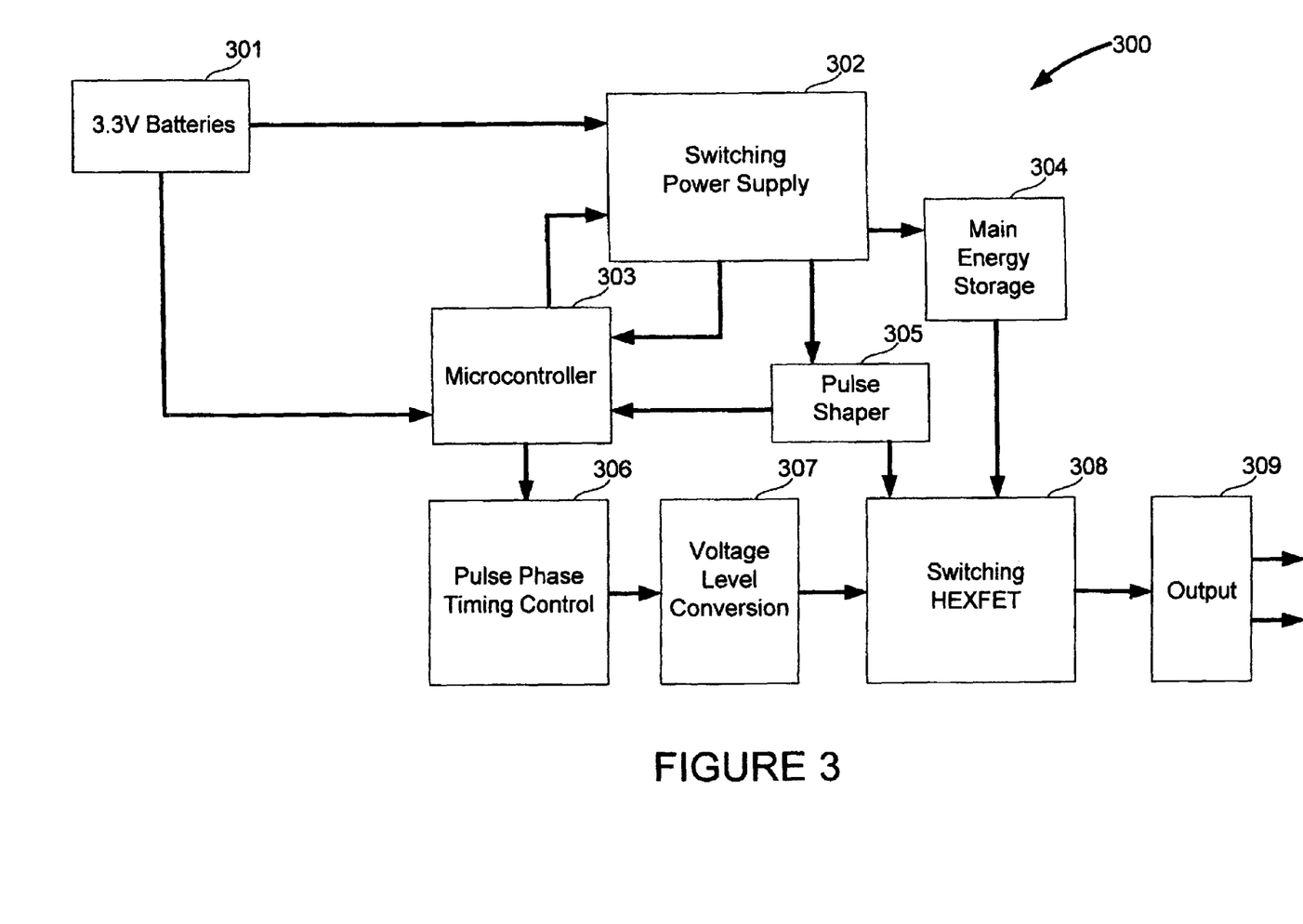
FIG. 3 is a block diagram of miniaturized circuitry according to a preferred embodiment of the present invention.

FIG. 3 depicts a block diagram of a preferred embodiment according to the present invention of a miniature control circuit 300. The miniature control circuit 300 produces waveforms that drive a generating device such as wire coils described above in FIG. 2. The miniature control circuit can be activated by any activation means such as an on/off switch. The miniature control circuit 300 has a power source such as a lithium battery 301. A preferred embodiment of the power source has an output voltage of 3.3 V but other voltages can be used. In another embodiment according to the present invention the power source can be an external power source such as an electric current outlet such as an AC/DC outlet, coupled to the present invention for example by a plug and wire. A switching power supply 302 controls voltage to a micro-controller 303. A preferred embodiment of the micro-controller 303 uses an 8 bit 4 MHz micro-controller 303 but other bit MHz combination micro-controllers may be used. The switching power supply 302 also delivers current to storage capacitors 304. A preferred embodiment of the present invention uses storage capacitors having a 220 uF output but other outputs can be used. The storage capacitors 304 allow high frequency pulses to be delivered to a coupling device such as inductors (Not Shown). The micro-controller 303 also controls a pulse shaper 305 and a pulse phase timing control 306. The pulse shaper 305 and pulse phase timing control 306 determine pulse shape, burst width, burst envelope shape, and burst repetition rate. An integral waveform generator, such as a sine wave or arbitrary number generator can also be incorporated to provide specific waveforms. A voltage level conversion sub-circuit 308 controls an induced field delivered to a target pathway structure. A switching Hexfet 308 allows pulses of randomized amplitude to be delivered to output 309 that routes a waveform to at least one coupling device such as an inductor. The micro-controller 303 can also control total exposure time of a single treatment of a target pathway structure such as a molecule, cell, tissue, and organ. The miniature control circuit 300 can be constructed to be programmable and apply a pulsing magnetic field for a prescribed time and to automatically repeat applying the pulsing magnetic field for as many applications as are needed in a given time period, for example 10 times a day. A preferred embodiment according to the present invention uses treatments times of about 10 minutes to about 30 minutes. The miniature control circuit 300 can also be integrated with a positioning device. The positioning device can also include at least one of a therapeutic surface, a therapeutic structure, and a therapeutic device, such as diathermy, ultrasound, TENS, massage, heat compress, cold compress, anatomical support surfaces, structures, and devices.

Figure 4:
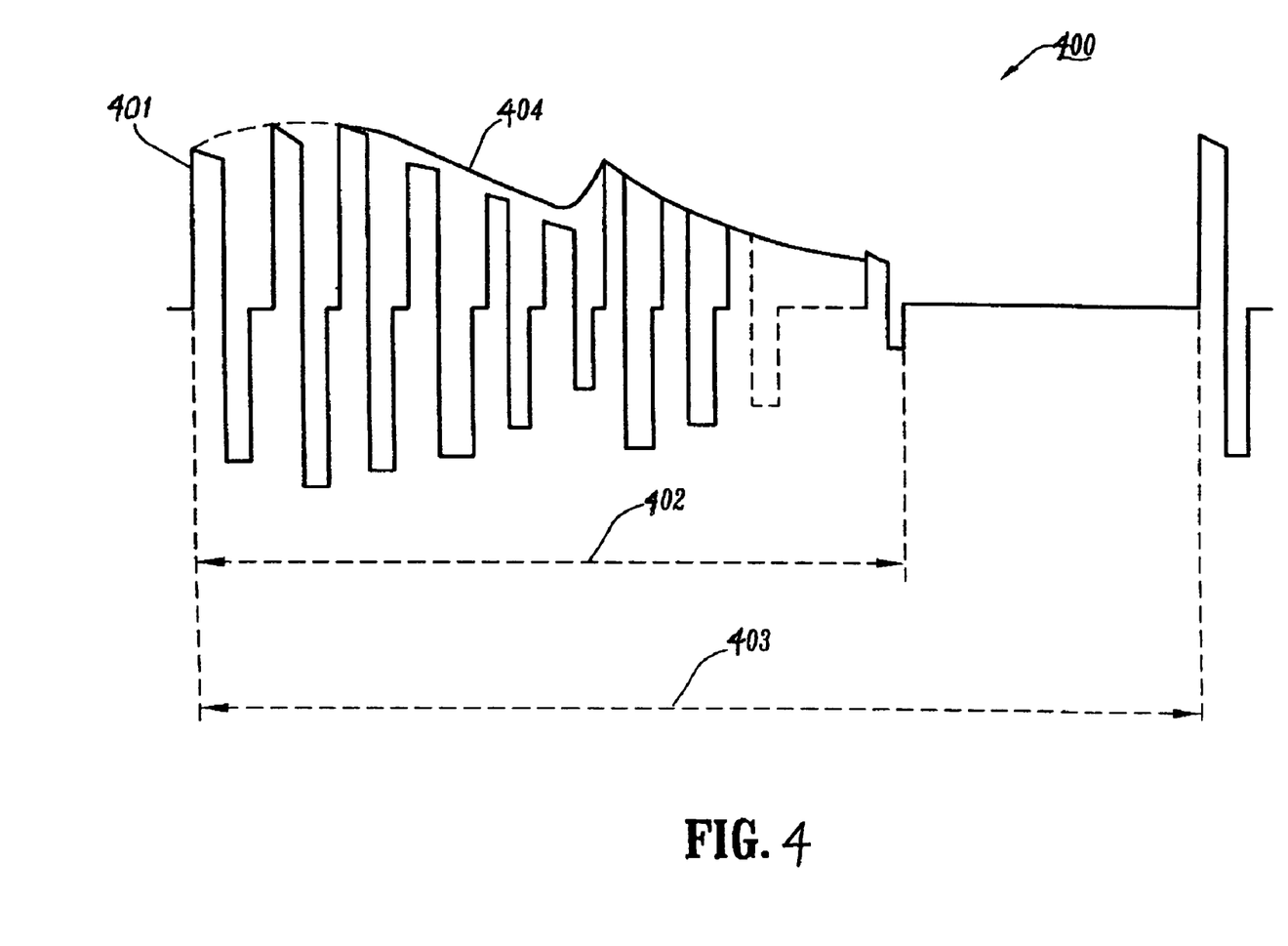
FIG. 4 depicts a waveform delivered to a target pathway structure according to a preferred embodiment of the present invention.
Figure 5:
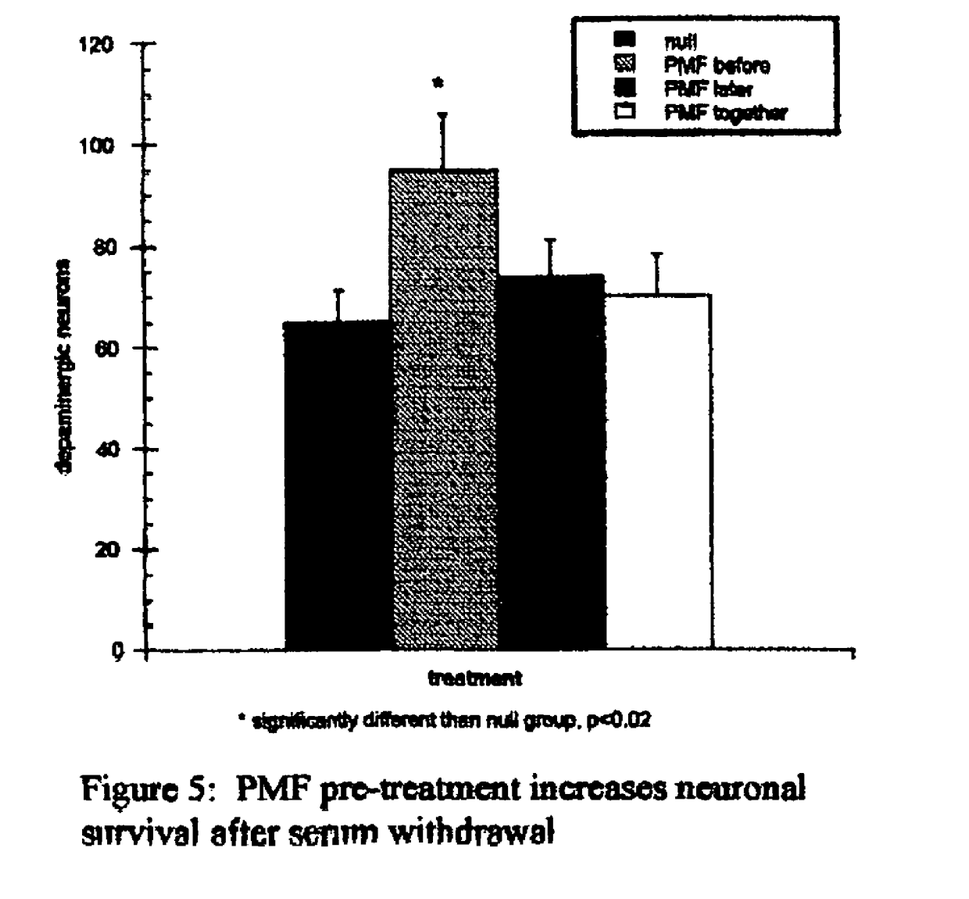
FIG. 5 is a bar graph illustrating PMF pre-treatment results.

Referring to FIG. 4 an embodiment according to the present invention of a waveform 400 is illustrated. A pulse 401 is repeated within a burst 402 that has a finite duration 403. The duration 403 is such that a duty cycle which can be defined as a ratio of burst duration to signal period is between about 1 to about $10^{-5}$. A preferred embodiment according to the present invention utilizes pseudo rectangular 10 microsecond pulses for pulse 401 applied in a burst 402 for about 10 to about 50 msec having a modified 1/f amplitude envelope 404 and with a finite duration 403 corresponding to a burst period of between about 0.1 and about 10 seconds.

EXAMPLE 1

The Power SNR approach for PMF signal configuration has been tested experimentally on calcium dependent myosin phosphorylation in a standard enzyme assay. The cell-free reaction mixture was chosen for phosphorylation rate to be linear in time for several minutes, and for sub-saturation $Ca^{2+}$ concentration. This opens the biological window for $Ca^{2+}$/CaM to be EMF-sensitive. This system is not responsive to PMF at levels utilized in this study if $Ca^{2+}$ is at saturation levels with respect to CaM, and reaction is not slowed to a minute time range. Experiments were performed using myosin light chain ("MLC") and myosin light chain kinase ("MLCK") isolated from turkey gizzard. A reaction mixture consisted of a basic solution containing 40 mM Hepes buffer, pH 7.0; 0.5 mM magnesium acetate; 1 mg/ml bovine serum albumin, 0.1% (w/v) Tween 80; and 1 mM EGTA12. Free $Ca^{2+}$ was varied in the 1-7 μM range. Once $Ca^{2+}$ buffering was established, freshly prepared 70 nM CaM, 160 nM MLC and 2 nM MLCK were added to the basic solution to form a final reaction mixture. The low MLC/MLCK ratio allowed linear time behavior in the minute time range. This provided reproducible enzyme activities and minimized pipetting time errors.

The reaction mixture was freshly prepared daily for each series of experiments and was aliquoted in 100 μL portions into 1.5 ml Eppendorf tubes. All Eppendorf tubes containing reaction mixture were kept at 0° C. then transferred to a specially designed water bath maintained at 37±0.1° C. by constant perfusion of water prewarmed by passage through a Fisher Scientific model 900 heat exchanger. Temperature was monitored with a thermistor probe such as a Cole-Parmer model 8110-20, immersed in one Eppendorf tube during all experiments. Reaction was initiated with 2.5 μM 32P ATP, and was stopped with Laemmli Sample Buffer solution containing 30 μM EBTA. A minimum of five blank samples were counted in each experiment. Blanks comprised a total assay mixture minus one of the active components $Ca^{2+}$, CaM, MLC or MLCK. Experiments for which blank counts were higher than 300 cpm were rejected. Phosphorylation was allowed to proceed for 5 min and was evaluated by counting 32P incorporated in MLC using a TM Analytic model 5303 Mark V liquid scintillation counter.

Figure 7:
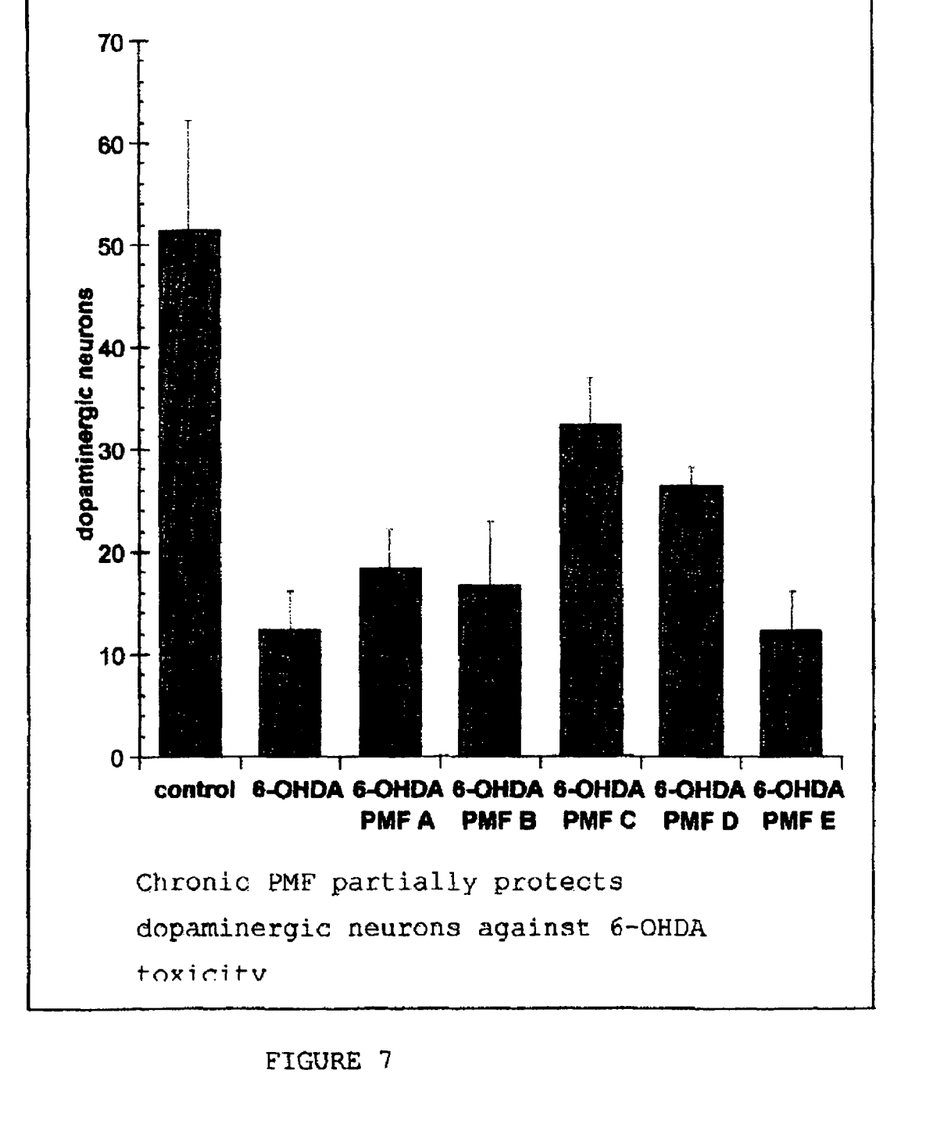
FIG. 7 is a bar graph illustrating chronic PMF results.

The signal comprised repetitive bursts of a high frequency waveform. Amplitude was maintained constant at 0.2 G and repetition rate was 1 burst/sec for all exposures. Burst duration varied from 65 μsec to 1000 μsec based upon projections of Power SNR analysis which showed that optimal Power SNR would be achieved as burst duration approached 500 μsec. The results are shown in FIG. 7 wherein burst width 701 in μsec is plotted on the x-axis and Myosin Phosphorylation 702 as treated/sham is plotted on the y-axis. It can be seen that the PMF effect on $Ca^{2+}$ binding to CaM approaches its maximum at approximately 500 μsec, just as illustrated by the Power SNR model.

These results confirm that a PMF signal, configured according to an embodiment of the present invention, would maximally increase myosin phosphorylation for burst durations sufficient to achieve optimal Power SNR for a given magnetic field amplitude.

EXAMPLE 2

According to an embodiment of the present invention use of a Power SNR model was further verified in an in vivo wound repair model. A rat wound model has been well characterized both biomechanically and biochemically, and was used in this study. Healthy, young adult male Sprague Dawley rats weighing more than 300 grams were utilized.

The animals were anesthetized with an intraperitoneal dose of Ketamine 75 mg/kg and Medetomidine 0.5 mg/kg. After adequate anesthesia had been achieved, the dorsum was shaved, prepped with a dilute betadine/alcohol solution, and draped using sterile technique. Using a #10 scalpel, an 8-cm linear incision was performed through the skin down to the fascia on the dorsum of each rat. The wound edges were bluntly dissected to break any remaining dermal fibers, leaving an open wound approximately 4 cm in diameter. Hemostasis was obtained with applied pressure to avoid any damage to the skin edges. The skin edges were then closed with a 4-0 Ethilon running suture. Post-operatively, the animals received Buprenorphine 0.1-0.5 mg/kg, intraperitoneal. They were placed in individual cages and received food and water ad libitum.

PMF exposure comprised two pulsed radio frequency waveforms. The first was a standard clinical PRF signal comprising a 65 μsec burst of 27.12 MHz sinusoidal waves at 1 Gauss amplitude and repeating at 600 bursts/sec. The second was a PRF signal reconfigured according to an embodiment of the present invention. For this signal burst duration was increased to 2000 μsec and the amplitude and repetition rate were reduced to 0.2 G and 5 bursts/sec respectively. PRF was applied for 30 minutes twice daily.

Tensile strength was performed immediately after wound excision. Two 1 cm width strips of skin were transected perpendicular to the scar from each sample and used to measure the tensile strength in $kg/mm^2$. The strips were excised from the same area in each rat to assure consistency of measurement. The strips were then mounted on a tensiometer. The strips were loaded at 10 mm/min and the maximum force generated before the wound pulled apart was recorded. The final tensile strength for comparison was determined by taking the average of the maximum load in kilograms per $mm^2$ of the two strips from the same wound.

The results showed average tensile strength for the 65 μsec 1 Gauss PRF signal was 19.3±4.3 $kg/mm^2$ for the exposed group versus 13.0±3.5 $kg/mm^2$ for the control group (p<0.01), which is a 48% increase. In contrast, the average tensile strength for the 2000 μsec 0.2 Gauss PRF signal, configured according to an embodiment of the present invention using a Power SNR model was 21.2±5.6 $kg/mm^2$ for the treated group versus 13.7±4.1 $kg/mm^2$ (p<0.01) for the control group, which is a 54% increase. The results for the two signals were not significantly different from each other.

These results demonstrate that an embodiment of the present invention allowed a new PRF signal to be configured that could be produced with significantly lower power. The PRF signal configured according to an embodiment of the present invention, accelerated wound repair in the rat model in a low power manner versus that for a clinical PRF signal which accelerated wound repair but required more than two orders of magnitude more power to produce.

EXAMPLE 3

This example illustrates the effects of PRF electromagnetic fields chosen via the Power SNR method on neurons in culture.

Primary cultures were established from embryonic days 15-16 rodent mesencephalon. This area is dissected, dissociated into single cells by mechanical trituration, and cells are plated in either defined medium or medium with serum. Cells are typically treated after 6 days of culture, when neurons have matured and developed mechanisms that render them vulnerable to biologically relevant toxins. After treatment, conditioned media is collected. Enzyme linked immunosorbent assays ("ELISAs") for growth factors such as Fibroblast Growth Factor beta ("FGFb") are used to quantify their release into the medium. Dopaminergic neurons are identified with an antibody to tyrosine hydroxylase ("TH"), an enzyme that converts the amino acid tyrosine to L-dopa, the precursor of dopamine, since dopaminergic neurons ate the only cells that produce this enzyme in this system. Cells are quantified by counting TH+ cells in perpendicular strips across the culture dish under 100× magnification.

Serum contains nutrients and growth factors that support neuronal survival. Elimination of serum induces neuronal cell death. Culture media was changed and cells were exposed to PMF (power level 6, burst width 3000 μsec, and frequency 1 Hz). Four groups were utilized. Group 1 used No PMF exposure (null group). Group 2 used Pre-treatment (PMF treatment 2 hours before medium change). Group 3 used Post-treatment (PMF treatment 2 hours after medium change). Group 4 used Immediate treatment (PMF treatment simultaneous to medium change).

Figure 6:
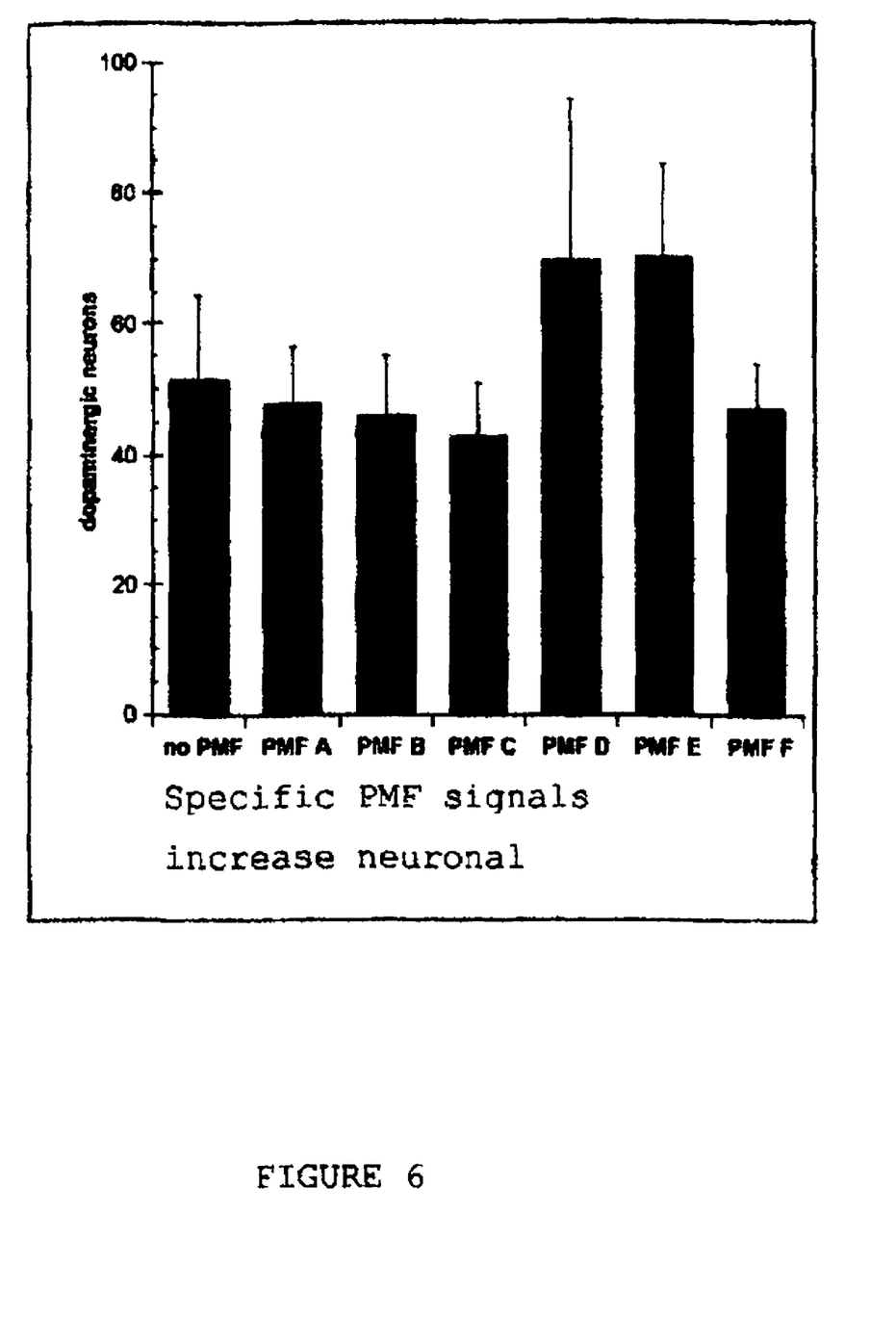
FIG. 6 is a bar graph illustrating specific PMF signal results.

Results demonstrate a 46% increase in the numbers of surviving dopaminergic neurons after 2 days when cultures were exposed to PMF prior to serum withdrawal. Other treatment regimes had no significant effects on numbers of surviving neurons. The results are shown in FIG. 6 where type of treatment is shown on the x-axis and number of neurons is shown on the y-axis.

FIG. 7, where treatment is shown on the x-axis and number of neurons is shown on the y-axis, illustrates that PMF signals D and E increase numbers of dopaminergic neurons after reducing serum concentrations in the medium by 46% and 48% respectively. Both signals were configured with a burst width of 3000 μsec, and the repetition rates are 5/sec and 1/sec, respectively. Notably, signal D was administered in a chronic paradigm in this experiment, but signal E was administered only once: 2 hours prior to serum withdrawal, identical to experiment 1 (see above), producing effects of the same magnitude (46% vs. 48%). Since the reduction of serum in the medium reduces the availability of nutrients and growth factors, PMF induces the synthesis or release of these factors by the cultures themselves.

This portion of the experiment was performed to illustrate the effects of PMF toxicity induced by 6-OHDA, producing a well-characterized mechanism of dopaminergic cell death. This molecule enters cells via high affinity dopamine transporters and inhibits mitochondrial enzyme complex I, thus killing these neurons by oxidative stress. Cultures were treated with 25 μM 6-OHDA after chronic, or acute PMF exposure paradigms. FIG. 8 illustrates these results, where treatment is shown on the x-axis and number of neurons is shown on the y-axis. The toxin killed approximately 80% of the dopaminergic neurons in the absence of PMF treatment. One dose of PMF (power=6; burst width=3000 μsec; frequency=1/sec) significantly increased neuronal survival over 6-OHDA alone (2.6-fold; $p \leq 0.02$). This result has particular relevance to developing neuroprotection strategies for Parkinson's disease, because 6-OHDA is used to lesion dopaminergic neurons in the standard rodent model of Parkinson's disease, and the mechanism of toxicity is similar in some ways to the mechanism of neurodegeneration in Parkinson's disease itself.

EXAMPLE 4

In this example electromagnetic field energy was used to stimulate neovascularization in an in vivo model. Two different signal were employed, one configured according to prior art and a second configured according to an embodiment of the present invention.

One hundred and eight Sprague-Dawley male rats weighing approximately 300 grams each, were equally divided into nine groups. All animals were anesthetized with a mixture of ketamine/acepromazine/Stadol at 0.1 cc/g. Using sterile surgical techniques, each animal had a 12 cm to 14 cm segment of tail artery harvested using microsurgical technique. The artery was flushed with 60 U/ml of heparinized saline to remove any blood or emboli. These tail vessels, with an average diameter of 0.4 mm to 0.5 mm, were then sutured to the transected proximal and distal segments of the right femoral artery using two end-to-end anastomoses, creating a femoral arterial loop. The resulting loop was then placed in a subcutaneous pocket created over the animal's abdominal wall/groin musculature, and the groin incision was closed with 4-0 Ethilon. Each animal was then randomly placed into one of nine groups: groups 1 to 3 (controls), these rats received no electromagnetic field treatments and were killed at 4, 8, and 12 weeks; groups 4 to 6, 30 min. treatments twice a day using 0.1 gauss electromagnetic fields for 4, 8, and 12 weeks (animals were killed at 4, 8, and 12 weeks, respectively); and groups 7 to 9, 30 min. treatments twice a day using 2.0 gauss electromagnetic fields for 4, 8, and 12 weeks (animals were killed at 4, 8, and 12 weeks, respectively).

Pulsed electromagnetic energy was applied to the treated groups using a device constructed according to an embodiment of the present invention. Animals in the experimental groups were treated for 30 minutes twice a day at either 0.1 gauss or 2.0 gauss, using short pulses (2 msec to 20 msec) 27.12 MHz. Animals were positioned on top of the applicator head and confined to ensure that treatment was properly applied. The rats were reanesthetized with ketamine/acepromazine/Stadol intraperitoneally and 100 U/kg of heparin intravenously. Using the previous groin incision, the femoral artery was identified and checked for patency. The femoral/tail artery loop was then isolated proximally and distally from the anastomoses sites, and the vessel was clamped off. Animals were then killed. The loop was injected with saline followed by 0.5 cc to 1.0 cc of colored latex through a 25-gauge cannula and clamped. The overlying abdominal skin was carefully resected, and the arterial loop was exposed. Neovascularization was quantified by measuring the surface area covered by new blood-vessel formation delineated by the intraluminal latex. All results were analyzed using the SPSS statistical analysis package.

The most noticeable difference in neovascularization between treated versus untreated rats occurred at week 4. At that time, no new vessel formation was found among controls, however, each of the treated groups had similar statistically significant evidence of neovascularization at 0 cm2 versus 1.42±0.80 cm2 ($p < 0.001$). These areas appeared as a latex blush segmentally distributed along the sides of the arterial loop. At 8 weeks, controls began to demonstrate neovascularization measured at 0.7±0.82 cm2. Both treated groups at 8 weeks again had approximately equal statistically significant ($p < 0.001$) outcroppings of blood vessels of 3.57±1.82 cm2 for the 0.1 gauss group and of 3.77±1.82 cm2 for the 2.0 gauss group. At 12 weeks, animals in the control group displayed 1.75±0.95 cm2 of neovascularization, whereas the 0.1 gauss group demonstrated 5.95±3.25 cm2, and the 2.0 gauss group showed 6.20±3.95 cm2 of arborizing vessels. Again, both treated groups displayed comparable statistically significant findings (p<0.001) over controls.

These experimental findings demonstrate that electromagnetic field stimulation of an isolated arterial loop according to an embodiment of the present invention increases the amount of quantifiable neovascularization in an in vivo rat model. Increased angiogenesis was demonstrated in each of the treated groups at each of the sacrifice dates. No differences were found between the results of the two gauss levels tested as predicted by the teachings of the present invention.

Having described embodiments for an integrated coil apparatus for therapeutically treating human and animal cells, tissues, and organs with electromagnetic fields and method for using same, it is noted that modifications and variations can be made by persons skilled in the art in light of the above teachings. It is therefore to be understood that changes may be made in the particular embodiments of the invention disclosed which are within the scope and spirit of the invention as defined by the appended claims.

What is claimed is:

1. A method for electromagnetic therapeutic treatment of animals and humans comprising the steps of:
   Configuring at least one waveform according to a mathematical model having at least one waveform parameter, said at least one waveform to be coupled to a target pathway structure;
   Choosing a value of said at least one waveform parameter to satisfy a Signal to Noise Ratio model so that said at least waveform is configured to be detectable in said target pathway structure above background activity in said target pathway structure;
   Generating an electromagnetic signal from said configured at least one waveform;
   Integrating at least one coupling device with a positioning device to be placed in proximity to said target pathway structure; and
   Coupling said electromagnetic signal to said target pathway structure using said at least one coupling device.

2. The method of claim 1, wherein said at least one waveform parameter includes at least one of a frequency component parameter that configures said at least one waveform to repeat between about 0.01 Hz and about 100 MHz, a burst amplitude envelope parameter that follows a mathematically defined amplitude function, a burst width parameter that varies at each repetition according to a mathematically defined width function, a peak induced electric field parameter varying between about 1 µV/cm and about 100 mV/cm in said target pathway structure according to a mathematically defined function, and a peak induced magnetic electric field parameter varying between about 1 µT and about 0.1 T in said target pathway structure according to a mathematically defined function.

3. The method of claim 2, wherein said defined amplitude function includes at least one of a 1/frequency function, a logarithmic function, a chaotic function, and an exponential function.

4. The method of claim 1, wherein said target pathway structure includes at least one of molecules, cells, tissues, organs, ions, and ligands.

5. The method of claim 1, further comprising the step of binding ions and ligands to regulatory molecules to enhance tissue growth, repair, and maintenance.

6. The method of claim 5, wherein said binding of ions and ligands includes modulating Calcium to Calmodulin binding.

7. The method of claim 5, wherein said binding of ions and ligands includes modulating growth factor production in target pathway structures.

8. The method of claim 5, wherein said binding of ions and ligands includes modulating cytokine production in target pathway structures.

9. The method of claim 5, wherein said binding of ions and ligands includes modulating growth factors and cytokines relevant to tissue growth, repair, and maintenance.

10. The method of claim 5, wherein said binding of ions and ligands includes modulating angiogenesis and neovascularization for growth, repair, and maintenance of target pathway structures.

11. The method of claim 5, wherein said binding of ions and ligands includes modulating angiogenesis and neovascularization for treatment of cerebrovascular disease.

12. The method of claim 5, wherein said binding of ions and ligands includes modulating growth factors and cytokines for treatment of sleep disorders.

13. The method of claim 5, wherein said binding of ions and ligands includes modulating angiogenesis and neovascularization for treatment of sleep disorders.

14. The method of claim 5, wherein said binding of ions and ligands includes modulation of the release of human growth hormone by increasing the length of deep sleep stages.

15. The method of claim 1, further comprising the step of applying pharmacological and herbal agents to target pathway structures for growth, repair, and maintenance of tissue.

16. The method of claim 15, wherein said pharmacological and herbal agents include at least one of topical drugs, topical creams, and topical ointments.

17. The method of claim 1, further comprising the step of applying pharmacological and herbal agents to target pathway structures for treatment of neurodegenerative diseases.

18. The method of claim 1, wherein said positioning device includes at least one of therapeutic surfaces, therapeutic structures, therapeutic devices, surgical dressings, anatomical supports, anatomical wraps, wound dressings, pads, seat cushions, mattress pads, shoes, wheelchairs, chairs, apparel, sporting goods and structures that can be placed in proximity to living tissue and cells.

19. The electromagnetic treatment apparatus of claim 18, wherein said apparel includes at least one of garments, fashion accessories, shoes, socks, and footware.

20. The method of claim 1, wherein said coupling device includes at least one of conductive thread and coil.

21. The method of claim 1, further comprising the step of applying of standard physical therapy modalities for treatment of a body area.

22. The method of claim 21, wherein standard physical therapy modalities includes at least one of heat, cold, compression, massage and exercise.

23. The method of claim 1, further comprising the step of simultaneously generating said electromagnetic signal to a plurality of said at least one coupling device.

24. The method of claim 23, wherein said electromagnetic signal is generated from at least one of, identically configured said at least one waveforms, and differently configured said at least one waveforms.

25. The method of claim 1, further comprising the step of sequentially generating an electromagnetic signal to a plurality of said at least one coupling device.

26. The method of claim 25, wherein said electromagnetic signal is generated from at least one of, identically configured said at least one waveforms, and differently configured said at least one waveforms.

27. The method of claim 1, further comprising the step of multiplexing an electromagnetic signal to a plurality of said at least one coupling device.

28. The method of claim 27, wherein said electromagnetic signal is generated from at least one of, identical at least one of said configured waveforms, and different at least one of said configured waveforms.

29. The method of claim 1, further comprising the step of using at least one of standard medical therapies and non-standard medical therapies adjunctively with said electromagnetic treatment inductive apparatus.

30. The method of claim 29, wherein standard medical therapies includes at least one of tissue transplants, and organ transplants.

31. The method of claim 1, further comprising the step of using at least one of standard physical therapies and non-standard physical therapies conjunctively with said electromagnetic treatment inductive apparatus.

32. The method of claim 31, wherein standard physical therapies includes at least one of ultrasound, negative pressure, positive pressure, heat, cold, massage, exercise, and acupuncture.

33. The method of claim 1, wherein the step of coupling said electromagnetic signal to said target pathway structure includes coupling to prevent loss and deterioration of cells and tissues.

34. The method of claim 1, wherein the step of coupling said electromagnetic signal to said target pathway structure includes coupling to augment cell and tissue activity.

35. The method of claim 1, wherein the step of coupling said electromagnetic signal to said target pathway structure includes coupling to increase cell population.

36. The method of claim 1, wherein the step of coupling said electromagnetic signal to said target pathway structure includes coupling to prevent neuron deterioration.

37. The method of claim 1, wherein the step of coupling said electromagnetic signal to said target pathway structure includes coupling to increase neuron population.

38. The method of claim 1, wherein the step of coupling said electromagnetic signal to said target pathway structure includes coupling to prevent adrenergic neuron deterioration.

39. The method of claim 1, wherein the step of coupling said electromagnetic signal to said target pathway structure includes coupling to increase adrenergic neuron population.

40. The method of claim 1, wherein the step of generating an electromagnetic signal from said configured at least one waveform includes generating said electromagnetic signal programmably.

41. An electromagnetic treatment apparatus for animals and humans comprising:

A waveform configuration means for configuring at least one waveform to be coupled to a target pathway structure according to a mathematical model having at least one waveform parameter capable of being chosen to satisfy a Signal to Noise Ratio model so that said at least one waveform is configured to be detectable in said target structure above background activity in said target pathway structure;

At least one coupling device connected to said waveform configuration means by at least one connecting means for generating an electromagnetic signal from said configured at least one waveform and for coupling said electromagnetic signal to said target pathway structure; and a positioning device wherein said at least one coupling device is integral to said positioning device.

42. The electromagnetic treatment apparatus of claim 41, wherein said at least one waveform parameter includes at least one of a frequency component parameter that configures said at least one waveform to repeat between about 0.01 Hz and about 100 MHz according to a mathematical function, a burst amplitude envelope parameter that follows a mathematically defined amplitude function, a burst width parameter that varies at each repetition according to a mathematically defined width function, a peak induced electric field parameter varying between about 1 µV/cm and about 100 mV/cm in said target pathway structure according to a mathematically defined function, and a peak induced magnetic electric field parameter varying between about 1 µT and about 0.1 T in said target pathway structure according to a mathematically defined function.

43. The electromagnetic treatment apparatus of claim 41, wherein said defined amplitude function includes at least one of a 1/frequency function, a logarithmic function, a chaotic function, and an exponential function.

44. The electromagnetic treatment apparatus of claim 41, wherein said target pathway structure includes at least one of molecules, cells, tissues, organs, ions, and ligands.

45. The electromagnetic treatment apparatus of claim 41, wherein the signal is inductively coupled to said target pathway structure wherein Calcium binding to Calmodulin is modulated.

46. The electromagnetic treatment apparatus of claim 41, wherein the signal is capacitively coupled to said target pathway structure wherein Calcium binding to Calmodulin is modulated.

47. The electromagnetic treatment apparatus of claim 41, wherein the signal is inductively coupled to said target pathway structure to modulate at least one of growth factor and cytokine production relevant to growth, repair, and maintenance of said target pathway structure.

48. The electromagnetic treatment apparatus of claim 47, wherein the growth factor includes at least one of fibroblast growth factors, platelet derived growth factors and interleukin growth factors.

49. The electromagnetic treatment apparatus of claim 41, wherein the signal is capacitively coupled to said target pathway structure to modulate at least one of growth factor and cytokine production relevant to growth, repair, and maintenance of said target pathway structure.

50. The electromagnetic treatment apparatus of claim 49, wherein the growth factor includes at least one of fibroblast growth factors, platelet derived growth factors and interleukin growth factors.

51. The electromagnetic treatment apparatus of claim 41, wherein the signal is capacitively coupled to said target pathway structure to modulate angiogenesis and neovascularization for the treatment of bone fractures.

52. The electromagnetic treatment apparatus of claim 41, wherein the signal is inductively coupled to said target pathway structure to modulate angiogenesis and neovascularization for the treatment of bone fractures.

53. The electromagnetic treatment apparatus of claim 41, wherein the signal is inductively coupled to said target pathway structure to modulate angiogenesis and neovascularization for the treatment of diseases.

54. The electromagnetic treatment apparatus of claim 41, wherein the signal is capacitively coupled to said target pathway structure to modulate angiogenesis and neovascularization for the treatment of diseases.

55. The electromagnetic treatment apparatus of claim 41, wherein the signal is inductively coupled to said target pathway structure to modulate angiogenesis and neovascularization for the treatment of vascular disease.

56. The electromagnetic treatment apparatus of claim 41, wherein the signal is capacitively coupled to said target pathway structure to modulate angiogenesis and neovascularization for the treatment of vascular disease.

57. The electromagnetic treatment apparatus of claim 41, wherein the signal is capacitively coupled to said target pathway structure to modulate angiogenesis and neovascularization for treatment of neurodegenerative diseases.

58. The electromagnetic treatment apparatus of claim 41, wherein the signal is inductively coupled to said target pathway structure to modulate angiogenesis and neovascularization for treatment of sleep disorders.

59. The electromagnetic treatment apparatus of claim 41, wherein the signal is capacitively coupled to said target pathway structure to modulate angiogenesis and neovascularization for treatment of sleep disorders.

60. The electromagnetic treatment apparatus of claim 41, wherein the signal is inductively coupled to said target pathway structure to modulate human growth factor production by increasing the periods of deep sleep.

61. The electromagnetic treatment apparatus of claim 41, wherein the signal is capacitively coupled to said pathway structure to modulate human growth factor production by increasing the periods of deep sleep.

62. The electromagnetic treatment apparatus of claim 41, wherein the electromagnetic treatment apparatus is configured to be lightweight, and portable.

63. The electromagnetic treatment apparatus of claim 41, wherein the positioning device includes at least one of therapeutic surfaces, therapeutic structures, therapeutic devices, surgical dressings, anatomical supports, anatomical wraps, wound dressings, pads, seat cushions, mattress pads, shoes, wheelchairs, chairs, apparel, sporting goods and structures that can be placed in proximity to living tissue and cells.

64. The electromagnetic treatment apparatus of claim 63, wherein said apparel includes at least one of garments, fashion accessories, shoes, socks, and footwear.

65. The electromagnetic treatment apparatus of claim 41, wherein said connecting means includes at least one of wire, wireless signal transmitting and receiving means, and direct connection means.

66. The electromagnetic treatment apparatus of claim 41, wherein the waveform configuration means is programmable.

67. The electromagnetic treatment apparatus of claim 41, wherein the waveform configuration means delivers at least one pulsing magnetic signal during a predetermined time.

68. The electromagnetic treatment apparatus of claim 41, wherein the waveform configuration means delivers at least one pulsing magnetic signal during a random time.

69. The electromagnetic treatment apparatus of claim 41, further comprising a delivery means for standard physical therapy modalities.

70. The electromagnetic treatment apparatus of claim 69, wherein said standard physical therapy modalities includes heat, cold, massage, and exercise.

71. The electromagnetic treatment apparatus of claim 41, further comprising a delivery means for pharmacological agents and herbal agents.

72. The electromagnetic treatment apparatus of claim 41, further comprising a delivery means for standard medical treatments.

73. The electromagnetic treatment apparatus of claim 72, wherein standard medical treatments includes at least one of treatments for neovascularization, angiogenesis, immune response for malignant and benign conditions, and transudation.

74. The electromagnetic treatment apparatus of claim 41, wherein said waveform configuration means is integrated with said positioning device.

75. The electromagnetic treatment apparatus of claim 41, wherein said positioning device is at least one of portable, implantable, disposable.

76. The electromagnetic treatment apparatus of claim 41, further comprising a plurality of at least one coupling device configured for simultaneously generating at least one electromagnetic signal from at least one configured waveform.

77. The electromagnetic treatment apparatus of claim 76, wherein said at least one configured waveform includes at least one of identical said at least one of configured waveforms, and different said at least one configured waveforms.

78. The electromagnetic treatment apparatus of claim 41, further comprising a plurality of at least one coupling device configured for sequentially generating at least one electromagnetic signal from at least one configured waveform.

79. The electromagnetic treatment apparatus of claim 78, wherein said at least one configured waveform includes at least one of identical said at least one of configured waveforms, and different said at least one configured waveforms.

80. The electromagnetic treatment apparatus of claim 41, further comprising a plurality of at least one coupling device configured for multiplexing at least one electromagnetic signal from at least one configured waveform.

81. The electromagnetic treatment apparatus of claim 80, wherein said at least one configured waveform includes at least one of, identical said at least one of configured waveforms, and different said at least one configured waveforms.

82. The electromagnetic treatment apparatus of claim 41, wherein the signal is inductively coupled to said target pathway structure.

83. The electromagnetic treatment apparatus of claim 41, wherein the signal is capacitively coupled to said target pathway structure.

84. The electromagnetic treatment apparatus of claim 41, wherein the signal is inductively coupled to said target pathway structure to prevent loss and deterioration of cells and tissues.

85. The electromagnetic treatment apparatus of claim 41, wherein the signal is capacitively coupled to said pathway structure to prevent loss and deterioration of cells and tissues.

86. The electromagnetic treatment apparatus of claim 41, wherein the signal is inductively coupled to said target pathway structure to augment cell activity.

87. The electromagnetic treatment apparatus of claim 41, wherein the signal is capacitively coupled to said pathway structure to augment cell activity.

88. The electromagnetic treatment apparatus of claim 41, wherein the signal is inductively coupled to said target pathway structure to increase cell population.

89. The electromagnetic treatment apparatus of claim 41, wherein the signal is capacitively coupled to said pathway structure to increase cell population.

90. The electromagnetic treatment apparatus of claim 41, wherein the signal is inductively coupled to said target pathway structure to prevent deterioration of neurons.

91. The electromagnetic treatment apparatus of claim 41, wherein the signal is capacitively coupled to said pathway structure to prevent deterioration of neurons.

92. The electromagnetic treatment apparatus of claim 41, wherein the signal is inductively coupled to said target pathway structure to increase neuron population.

93. The electromagnetic treatment apparatus of claim 41, wherein the signal is capacitively coupled to said pathway structure to increase neuron population.

94. The electromagnetic treatment apparatus of claim 41, wherein the signal is inductively coupled to said target pathway structure to prevent deterioration of adrenergic neurons.

95. The electromagnetic treatment apparatus of claim 41, wherein the signal is capacitively coupled to said pathway structure to prevent deterioration of adrenergic neurons.

96. The electromagnetic treatment apparatus of claim 41, wherein the signal is inductively coupled to said target pathway structure to increase adrenergic neuron population.

97. The electromagnetic treatment apparatus of claim 41, wherein the signal is capacitively coupled to said pathway structure to increase adrenergic neuron population.

98. The electromagnetic treatment apparatus of claim 41, wherein said waveform configuration means is programmable.

* * * * *